(12) United States Patent
Pelletier et al.

(10) Patent No.: US 10,648,328 B2
(45) Date of Patent: May 12, 2020

(54) SAMPLE PHASE QUALITY CONTROL

(71) Applicant: Halliburton Energy Services, Inc., Houston, TX (US)

(72) Inventors: Michael T. Pelletier, Houston, TX (US); Christopher Michael Jones, Houston, TX (US); Darren Gascooke, Houston, TX (US); Anthony H. Van Zuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/061,631

(22) PCT Filed: Dec. 29, 2016

(86) PCT No.: PCT/US2016/069325
§ 371 (c)(1),
(2) Date: Jun. 12, 2018

(87) PCT Pub. No.: WO2018/125168
PCT Pub. Date: Jul. 5, 2018

(65) Prior Publication Data
US 2020/0003053 A1    Jan. 2, 2020

(51) Int. Cl.
*E21B 49/08* (2006.01)
*E21B 47/06* (2012.01)
(Continued)

(52) U.S. Cl.
CPC ............ *E21B 49/081* (2013.01); *E21B 47/06* (2013.01); *E21B 47/065* (2013.01); *E21B 49/10* (2013.01);
(Continued)

(58) Field of Classification Search
CPC ...... E21B 49/081; E21B 47/065; E21B 47/06; E21B 47/12; E21B 49/086; G01N 33/2823; G01N 25/00
See application file for complete search history.

(56) References Cited

U.S. PATENT DOCUMENTS

| 4,033,186 A | 7/1977 | Bresie |
| 4,195,349 A | 3/1980 | Balkanli |

(Continued)

FOREIGN PATENT DOCUMENTS

WO    2013002803    1/2013

OTHER PUBLICATIONS

International Search Report and Written Opinion for Application No. PCT/US16/69325 dated Sep. 5, 2017.
(Continued)

*Primary Examiner* — Brad Harcourt
(74) *Attorney, Agent, or Firm* — Benjamin Fite; C. Tumey Law Group PLLC

(57) ABSTRACT

Systems and methods for subterranean formation testing. A method may include: lowering a formation testing tool into a subterranean formation, wherein the formation testing tool may include memory, a pump, a formation probe, at least two sample chambers, wherein the at least two sample chambers may include probes to measure pressure and temperature; extracting a fluid from the subterranean formation with the pump and the formation probe; flowing the fluid into the at least two sample chambers with the pump; storing pressure and temperature data of the fluid in the memory; and removing the at least two sample chambers from the formation testing tool.

19 Claims, 4 Drawing Sheets

(51) Int. Cl.
    *E21B 49/10*     (2006.01)
    *G01N 25/00*     (2006.01)
    *G01N 33/28*     (2006.01)
    *E21B 47/12*     (2012.01)

(52) U.S. Cl.
    CPC ......... *G01N 25/00* (2013.01); *G01N 33/2823* (2013.01); *E21B 47/12* (2013.01); *E21B 49/086* (2013.01)

(56) References Cited

U.S. PATENT DOCUMENTS

| | | |
|---|---|---|
| 4,976,142 A | 12/1990 | Perales |
| 5,027,637 A | 7/1991 | Umetsu |
| 5,627,770 A | 5/1997 | Barbier et al. |
| 5,635,631 A | 6/1997 | Yesudas et al. |
| 7,062,958 B2 | 6/2006 | Diakonov et al. |
| 7,079,242 B2 | 7/2006 | Bordelon |
| 7,083,009 B2 | 8/2006 | Paluch et al. |
| 7,155,990 B2 | 1/2007 | Gilbert |
| 8,061,213 B2 | 11/2011 | Kurtz et al. |
| 8,215,388 B2 | 7/2012 | Van Zuilekom et al. |
| 8,398,301 B2 | 3/2013 | Madhavan et al. |
| 8,731,848 B2 | 5/2014 | Jones et al. |
| 8,921,768 B2 | 12/2014 | Jones et al. |
| 9,249,659 B2 | 2/2016 | Pelletier et al. |
| 2005/0028973 A1 | 2/2005 | Paluch et al. |
| 2008/0087470 A1 | 4/2008 | Villareal et al. |
| 2010/0018287 A1 | 1/2010 | Iakimov |
| 2010/0252258 A1* | 10/2010 | Pelletier .................. E21B 49/10 166/264 |
| 2013/0311099 A1 | 11/2013 | Eyuboglu et al. |
| 2013/0319102 A1* | 12/2013 | Ringgenberg .......... E21B 49/10 73/152.28 |
| 2016/0011331 A1 | 1/2016 | Perkins et al. |
| 2016/0215617 A1 | 7/2016 | Samec et al. |

OTHER PUBLICATIONS

French Search Report for Application No. PAT2528385FR00, dated May 6, 2019.

* cited by examiner

SAMPLE PHASE QUALITY CONTROL

BACKGROUND

Reservoir fluid samples may be needed for a variety of reasons. Reservoir fluid samples may be taken from a subterranean formation and then analyzed to establish their physical and chemical properties, such as hydrocarbon type and pressure, volume and temperature (PVT) behavior of the reserves in place. These properties may help in planning efficient extraction of the hydrocarbons. A set of measurements performed on a fluid sample from a hydrocarbon reservoir may include PVT relationships, viscosity, composition, gas/oil ratio (GOR), differential vaporization, and multistage separation tests. Fluid samples may also provide information needed to aid in planning and special treatments that may be required for production, such as hydrogen sulfide removal, waxing tendencies, asphaltene content, metallurgy and refining trials. Asphaltene precipitation may produce tar-like solids that may come out of suspension in crude oil when pressure is reduced within the formation, in production tubing and in surface facilities. Therefore, asphaltene content may be an important parameter in choosing optimal completion designs.

The fluid samples may be taken by formation testing tools and placed into sample cylinders of the formation testing tool. Standard un-cushioned wireline sample chambers may risk phase change as the temperature of the system changes. Although, the integrity of the sample may be checked at surface, and once again at the laboratory prior to opening, the integrity of the sample may not currently be checked at ocean floor conditions or during transport to the laboratory. Also, although nitrogen cushioned cylinders may be more resistant to phase change, for low GOR high pressure samples, such as found in the turbidite sands of the Gulf of Mexico, maintaining single phase may not be guaranteed. Additionally, although the integrity of the sample may be checked at single points at surface, and the laboratory, often the sample is not quality controlled ("QC").

BRIEF DESCRIPTION OF THE DRAWINGS

These drawings illustrate certain aspects of some examples of the present disclosure, and should not be used to limit or define the disclosure.

DETAILED DESCRIPTION

This disclosure may generally relate to systems and methods for QC of downhole fluid sampling. The present disclosure may include embedding a memory module retaining temperature data and pressure data within the sample chamber or sample valve, to guarantee the integrity of the sample from the reservoir to the laboratory. Additionally, the memory module may serve as a validation to laboratory reconstitution conditions and flash conditions. Asphaltene phase change may also be of concern and may also be detected with the same equipment, or enhanced with slight modification. QC of asphaltene precipitation may be of concern to operators especially since once precipitated, they may not be fully reconstituted by a laboratory back into solution. An asphaltene precipitation point may provide much more than just QC, as detection of a precipitation point may be of value to an operator preparing for flow assurance issues and calculating economic viability of assets.

Figure 1:
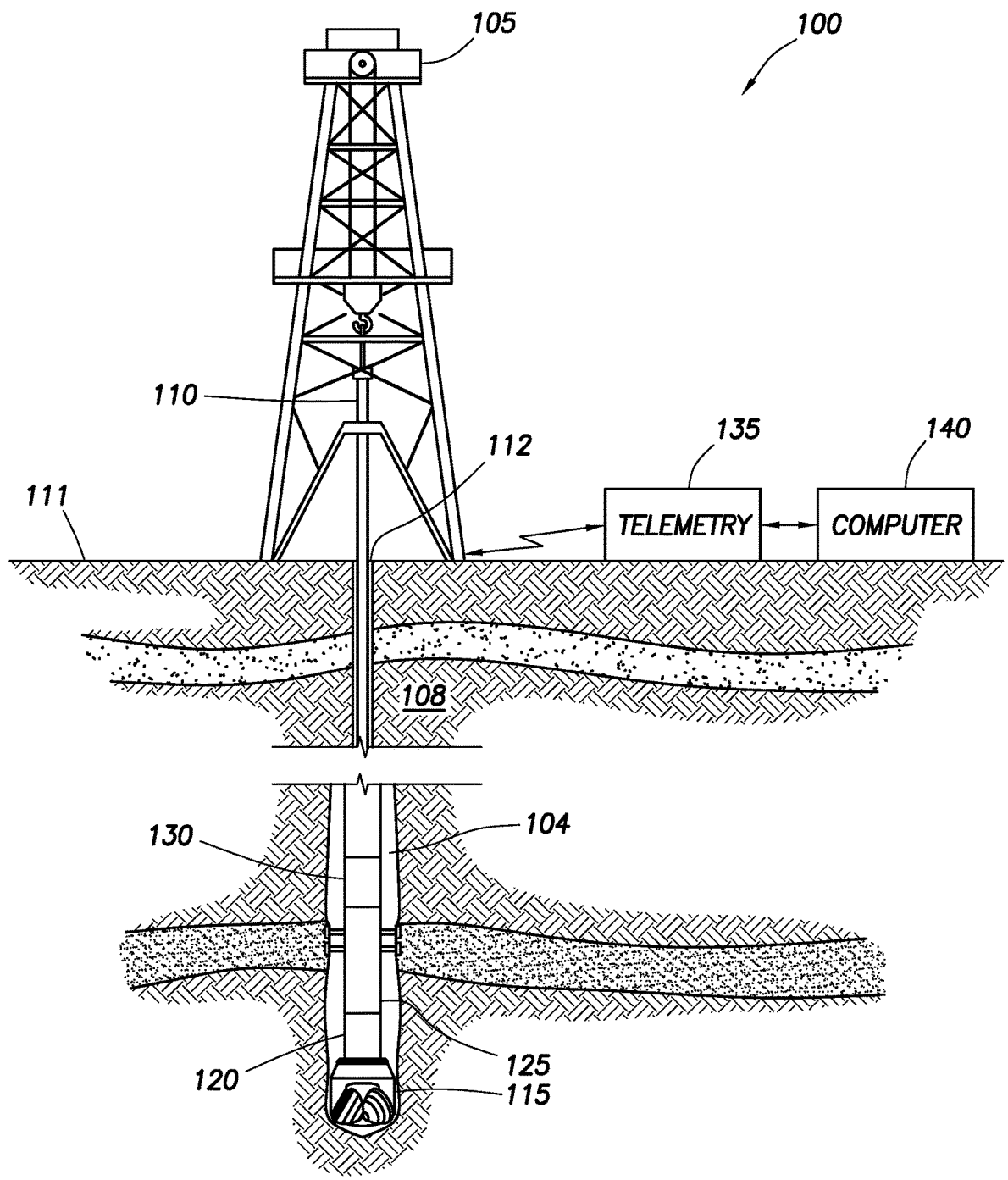
FIG. 1 illustrates a logging while drilling environment.

FIG. 1 illustrates an example environment 100, which may include a derrick 105 positioned on surface 111 from which a drill string 110 is suspended in a borehole 112 positioned in subterranean formation 108. The volume within the borehole 112 around the drill string 110 may be the annulus 114. The drill string 110 may include a drill bit 115, a variety of actuators and sensors, shown schematically by element 120, a formation testing tool 125 and a telemetry section 130, through which the downhole equipment communicates with a surface telemetry system 135. A computer 140 may include input/output devices, memory, storage, and network communication equipment, including equipment necessary to connect to the Internet, receive data from the downhole equipment and send commands to the downhole equipment.

Figure 4:
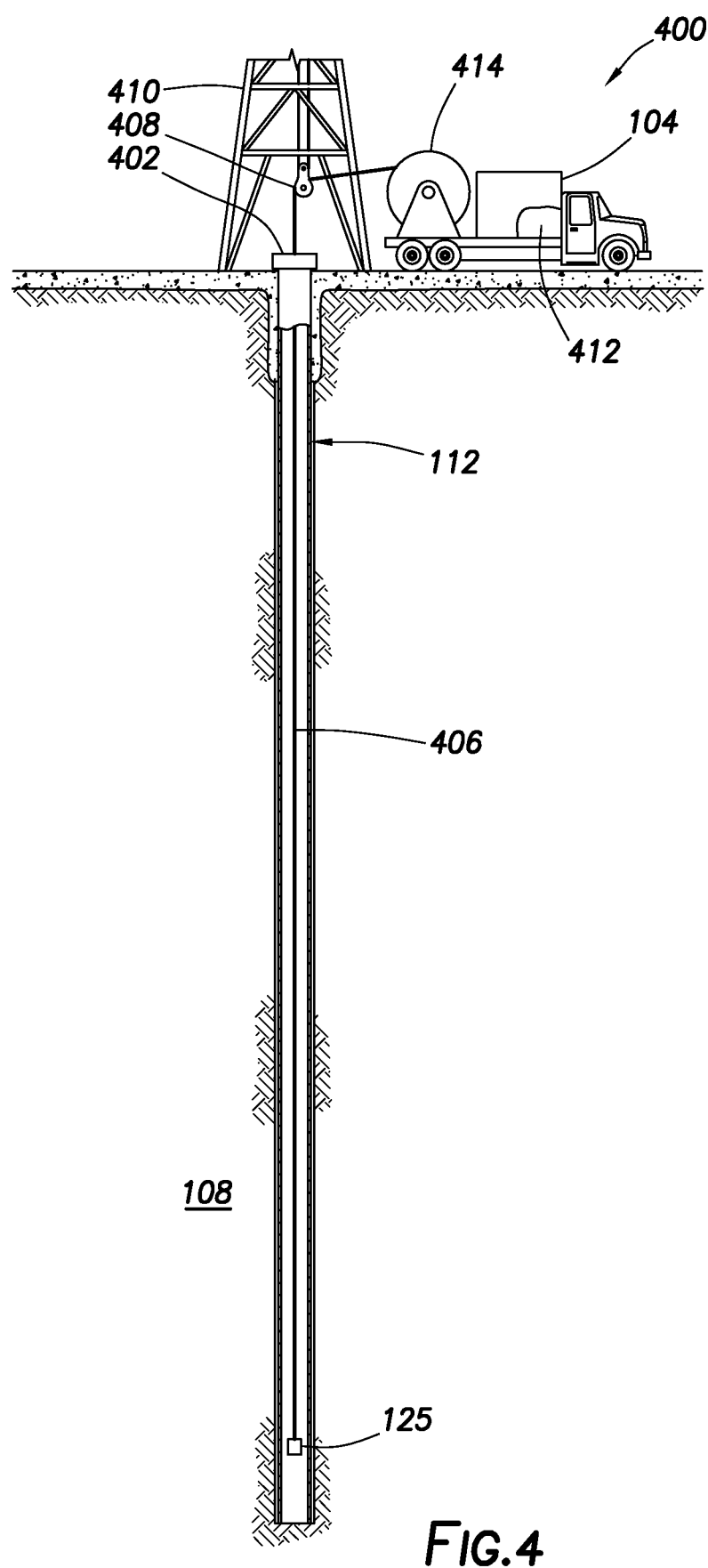
FIG. 4 is a schematic illustration of a wireline environment.

It should be noted that although FIG. 1 illustrates formation testing tool 125 as a measurement-while-drilling tool or logging-while-drilling tool, formation testing tool 125 may also be utilized on a conveyance, such as, a wireline (shown on FIG. 4).

The equipment and techniques described herein may also be useful in a wireline or slickline environment. For example, the formation testing tool 125 may be lowered into the borehole 112 using wired drill pipe, wireline, coiled tubing (wired or unwired), or slickline.

In a measurement-while-drilling or logging-while-drilling environment, such as that shown in FIG. 1, power for the formation testing tool 125 may be provided by a battery, by a mud turbine, or through a wired pipe from the surface, or through some other conventional means. In a wireline or slickline environment, power may be provided by a battery or by power provided from the surface through the wired drill pipe, wireline, coiled tubing, or slickline, or through some other conventional means.

In certain systems and methods, the drilling equipment may not be on dry land, as shown in FIG. 1 but may be on a wetland or at sea. In such an environment, the derrick 105 (or another piece of equipment that performs the function of the derrick) may be located on a drilling platform, such as a semi-submersible drilling rig, a drill ship, or a jack-up drilling rig. The drill string 110 may extend from the derrick 105 through the water, to the sea floor, and into the subterranean formation 108.

Figure 2:
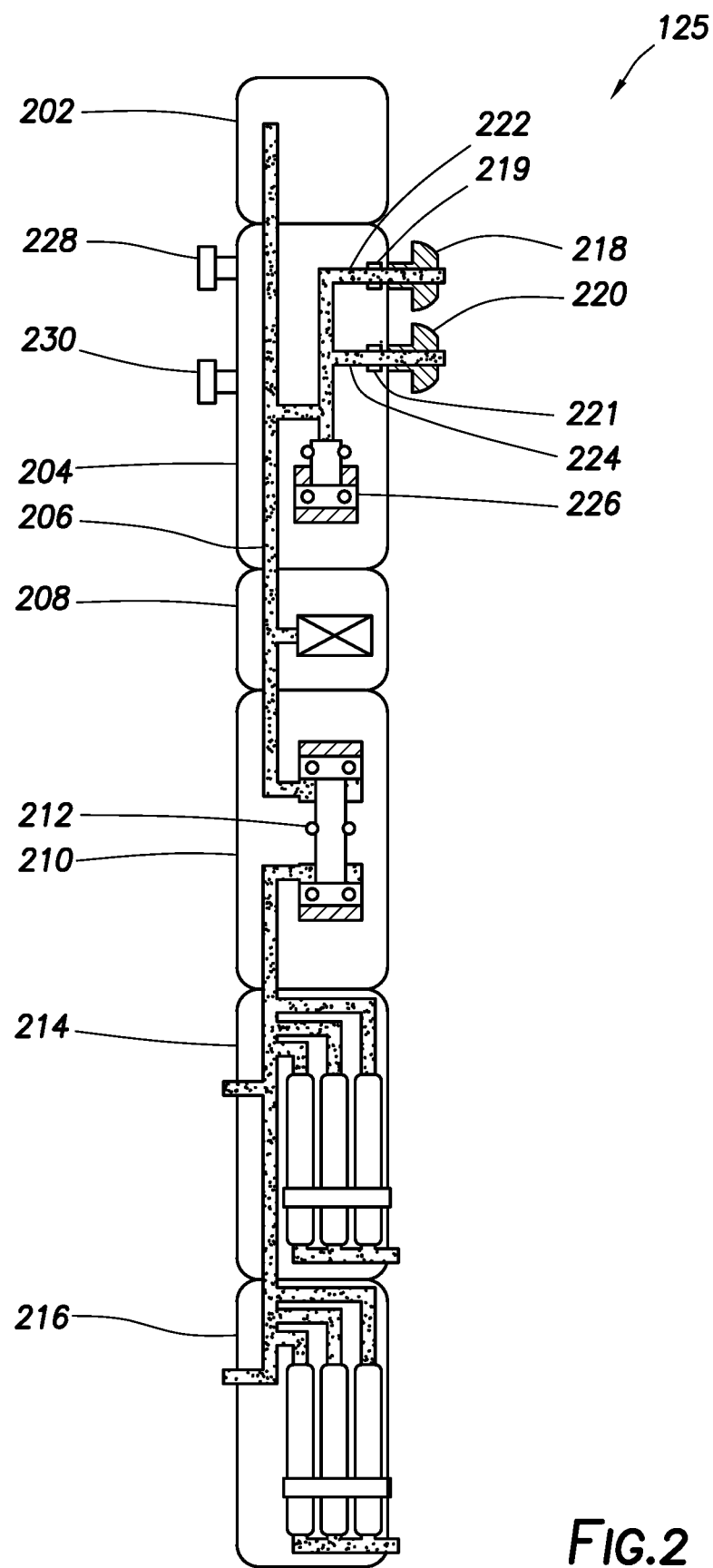
FIG. 2 is a schematic illustration of a formation testing tool.

Referring to FIGS. 1 and 2, the formation testing tool 125 may include a power telemetry section 202 through which the formation testing tool 125 may communicate with other actuators and sensors 120 in the drill string 110, the drill string's telemetry section 130, and/or directly with the surface telemetry system 135. In one embodiment, the power telemetry section 202 may also be the port through which the various actuators (e.g. valves) and sensors (e.g., temperature and pressure sensors) in the formation testing tool 125 are controlled and monitored. The power telemetry section 202 may include a computer that may exercise control and monitoring functions. The control and monitoring functions may be performed by a computer in another part of the drill string (not shown) or by the computer 140 on the surface.

The formation testing tool 125 may include a formation probe section 204, which may extract fluid from the reservoir, as described in more detail below, and may deliver it to a channel 206 that may extend from one end of the formation testing tool 125 to the other. The channel 206 may be connected to other tools. The formation testing tool 125 may also include a quartz gauge section 208, which may include sensors to allow measurement of properties, such as temperature and pressure, of the fluid in the channel 206. The formation testing tool 125 may include a flow-control pump-out section 210, which may include a high-volume bidirectional pump 212 for pumping fluid through the channel 206. The formation testing tool 125 may include two sample chamber sections 214, 216, which are described in more detail below. Alternatively, the formation testing tool 125 may include more or less than two sample chamber sections 214, 216.

The formation probe section 204 may include at least one formation probe (e.g., formation probes 218, 220) which may extend from the formation testing tool 125 and press against the borehole wall, as shown in FIG. 1.

Figure 3:
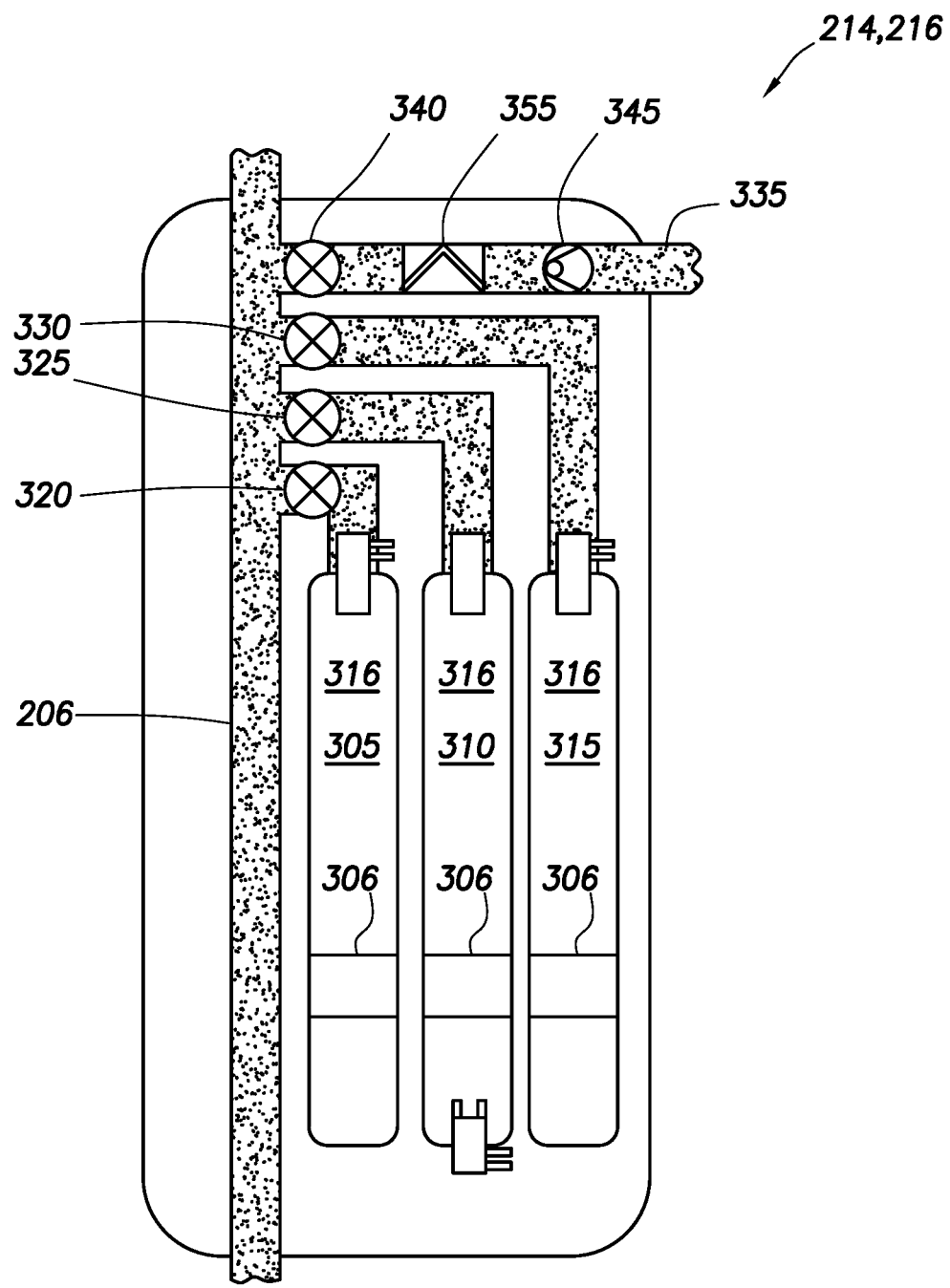
FIG. 3 is a schematic illustration of a multi-chamber section of a formation testing tool.

Referring back to FIG. 2, probe channels 222, 224 may connect the probes 218, 220 to the channel 206. The high-volume bidirectional pump 212 may be used to pump fluids from the reservoir, through the probe channels 222, 224 and to the channel 206. Alternatively, a low volume pump 226 may be used for this purpose. Two standoffs or stabilizers 228, 230 may hold the formation testing tool 125 in place as the probes 218, 220 press against the borehole wall. The probes 218, 220 and stabilizers 228, 230 may be retracted when the tool is in motion and is extended to sample the formation fluids. With additional reference to FIG. 3, the sample chamber sections 214, 216 may include multiple sample chambers 305, 310, 315. While FIGS. 2 and 3 show the sample chamber sections 214, 216 having three sample chambers 305, 310, 315, it will be understood that the sample chamber sections 214, 216 can have any number of sample chambers. It will also be understood that sample chamber section 214 can have a different number of sample chambers than sample chamber section 216. The sample chambers 305, 310, 315 may be coupled to the channel 206 through respective chamber valves 320, 325, 330. Reservoir fluid may be directed from the channel 206 to a selected one of sample chambers 305, 310, 315 by opening the appropriate chamber valve. For example, reservoir fluid may be directed from the channel 206 to sample chamber 305 by opening chamber valve 320; reservoir fluid may be directed from the channel 206 to sample chamber 310 by opening chamber valve 325; and reservoir fluid may be directed from the channel 206 to sample chamber 315 by opening chamber valve 330. When one chamber valve is open, the others may be closed. The sample chamber sections 214, 216 may include a path 335 from the channel 206 to the annulus 114 through a valve 340. Valve 340 may be open during the draw-down period when the formation tester is clearing mud cake, drilling mud, and other contaminants into the annulus before clean formation fluid is directed to one of the sample chambers 305, 310, 315. A check valve 345 may prevent fluids from the annulus 114 from flowing back into the channel 206 through the path 335.

Each of sample chambers 305, 310, 315 may be a standard un-cushioned cylinder or a nitrogen cushioned cylinder and may include sample fluid sections 316. Each sample chamber 305, 310, 315 may have any suitable volume, including a volume of about 0.5 liters to about 2 liters or about one liter, and include sample fluid sections 316. Although three sample chambers are illustrated, more or less than three sample chambers may be utilized. A sample obtained at bottom hole reservoir conditions may be of greater temperature and pressure than either surface conditions or seafloor conditions. As such, the sample may thermally contract as it is brought to the surface 111 (e.g., FIG. 1). Single phase pressure expansion of the sample may counter the effects of temperature volume depletion to an extent, however, for practically all liquid phase samples, the total effects of temperature depletion may be larger than pressure compensation. Two techniques may be designed to overcome this issue. First, the sample may be over pressurized at bottom hole conditions up to the lesser of either the sample rating or the pump capacity. Various pump capacities exist, but about 4,000 psi to about 8,000 psi may be utilized. This over pressurization may allow for extra pressure expansion potential. Secondly, one or more of the sample chambers 305, 310, 315 may be cushioned by a compensating force acting on a piston of the respective sample chamber 305, 310, or 315 to apply additional backing pressure to the sample. The "spring" (gas spring/gas buffer/gas cushion) may usually be enacted by nitrogen, which may balance the pressure on both sides of the piston. Because gas has a larger expansion coefficient than liquid samples (nitrogen being larger than most "real" gases), the pressure compensation for temperature may be more favorable than for a liquid. However, initial charges of nitrogen into sample chambers 305, 310, 315 may be limited practically to about 3,000 psi to about 6,000 psi, meaning that for very high pressure wells above 15,000 psi, the nitrogen may not be sufficient for some types of samples and thermal changes. Pre job planning may routinely estimate the effectiveness of phase stability during sampling and transport, however, assumptions may be made regarding the sample type including fluid properties such as phase behavior of the sample, thermal coefficient of expansion curve, compressibility curve for the sample, and the bubble point of the sample.

The present disclosure may seek to validate phase integrity of a sample from bottom hole through transport to the laboratory by recording the temperature and pressure of the sample as a history in memory from bottom hole to the laboratory.

As illustrated in FIG. 3, sample chambers 305, 310 may be nitrogen cushioned cylinders and sample chamber 315 may be a standard un-cushioned cylinder.

For a standard chamber (e.g., sample chamber 315), the volume of the cylinder (e.g., 1 liter), which may be calibrated and stored within a memory device (e.g., memory 303) for either the temperature sensor or pressure sensor or both. Any volume change of the cylinder with respect to temperature or pressure may also be obtained.

For a nitrogen-cushioned cylinder (e.g., sample chambers 305, 310 with a cylinder volume of 1 liter), the volume of the sample section of the cylinder changes with temperature and pressure. However, since the volume of nitrogen is known as a function of temperature and pressure for initial conditions, the volume change of the cylinder may be calculated for any temperature and pressure. Also, cylinder volume change effects independent of nitrogen volume changes may be calibrated. Both temperature and pressure volume changes may be smooth monotonic functions for single phase liquids, until a phase change is encountered. At a phase change, the first derivative of the curve is technically discontinuous (i.e., different slopes before and after the phase change).

For a standard cylinder (e.g., sample chamber 315), plotting the pressure as a function of temperature may be detected when the pressure change with temperature is discontinuous in the first derivative. Effectively, the sample may generate its own gas cushion as the sample drops below the bubble point.

For a nitrogen-cushioned cylinder (e.g., sample chambers 305, 310), the change in volume (calculated by the temperature and pressure of the sample) may be plotted as a function of the pressure (standard bubble point curve dimensions). The phase change may be detected by discontinuity of the first derivative of the curve. Known load volume on nitrogen (N), at temperature (T) and pressure (P) may give a known mass. At downhole conditions T and P, volume of nitrogen may be known. A sample may be pumped into a system (e.g., sample chamber). The total volume available may be known, the known volume of the sample may become a system volume minus nitrogen volume (where the variation in nitrogen's volume with temperature and pressure may be known). Measuring temperature and piston position enables a calculation of pressure within a vessel. If temperature and pressure are known, nitrogen volume may be calculated. From the system volume, the sample volume may be calculated by a difference between the system volume and nitrogen volume. Deviations for the known volumes may indicate either phase change or a leak.

It should be noted that the discontinuity of the curve in the first derivative may sometimes be blurred. There may be detection methods to detect a significant change, such as, but not limited to, a spike in the second derivative. It should also be noted that although two representative curves for each of the standard cylinder (e.g., sample chamber 315) and nitrogen-cushioned cylinder (e.g., sample chambers 305, 310) were described, other derivations of an equation of state may provide equivalent detection methods for a phase change.

Although, a phase change is undesirable, if detected, a point on the phase envelope for the curve is defined, in conjunction with a bubble point which may be measured at reservoir conditions. In addition, if a compressibility is measured downhole, and then again at surface temperature, then the thermal contraction portion of the samples volume/pressure change may be separated from the compressibility expansion for a nitrogen-cushioned cylinder. With measured density at reservoir conditions, and density at the surface temperature and corresponding pressure, equation of state utilizing downhole composition for the sample may be further refined. Even if the sample does not undergo a phase change in transit to the surface 111 (e.g., FIG. 1), the PVT (pressure-volume-temperature) measurement for a nitrogen-cushioned cylinder or PT (pressure-temperature) measurements for a standard cylinder could still improve an equation of state definition for the sample. Fluid properties (e.g., interfacial tension, phase behavior, compressibility, thermal expansion) obtained with the standard cylinder (e.g., sample chamber 315) may be compared (for QC) to the calculated fluid properties from the nitrogen-cushioned cylinder (e.g., sample chambers 305, 310). Sample chambers 305, 310 and 315 may include probes 307. Probes 307 may include memory 303 and may be embedded just below a chamber valve (e.g., chamber valves 320, 325, and/or 330) of a sample chamber (e.g., sample chambers 305, 310, and/or 315) and/or in a nitrogen filled section of a sample chamber (e.g., section 308 of sample chamber 310). Memory 303 may include volatile memory and/or non-volatile memory. Volatile memory may include computer memory that requires power to maintain the stored information (e.g., data regarding time, pressure, volume, and temperature of a sample fluid). Volatile memory is either static RAM (SRAM) or dynamic RAM (DRAM). SRAM retains its contents as long as the power is connected and is easy for interfacing, but uses six transistors per bit. Dynamic RAM is more complicated for interfacing and control, needing regular refresh cycles to prevent losing its contents, but uses only one transistor and one capacitor per bit. Non-volatile memory may include computer memory that can retain the stored information (e.g., data regarding time and pressure, volume, and temperature of a sample fluid) even when not powered. Examples of non-volatile memory include read-only memory (ROM), flash memory, magnetic computer storage devices (e.g. hard disk drives, floppy disks and magnetic tape) and/or optical discs.

Additionally, sample chambers 305, 310 may each include nitrogen filled section 308 and pistons 306. Sample chambers 305, 310 may be cushioned by a compensation force acting on the pistons 306 to apply additional backing pressure to the sample. The "spring" (gas spring/gas buffer/gas cushion) may be enacted by a nitrogen cushion, which may balance the pressure on both sides of the pistons 306. Because gas has a larger expansion coefficient than liquid samples (nitrogen being larger than most "real" gases), the pressure compensation for temperature may be more favorable than for a liquid. Initial charges of nitrogen into sample chambers 305, 310 may be limited practically to about 3,000 psi to about 6,000 psi.

Pistons 306 may include magnets 309. The position of the magnets 309 may be measured relative to each end (e.g., top 318 and bottom 319) of the sample chambers 305, 310, and equations of state may be used to calculate various sample properties such as, for example, interfacial tension, thermal expansion, compressibility, and phase behavior. Pistons 306 may move linearly from top 318 to bottom 319 (or from bottom 319 to top 318), however, pistons 306 may be locked into place thereby preventing movement of the pistons 306. Also, accelerometers 314 may be placed on the pistons 306 to monitor movement of the pistons 306 (e.g., jarring of the sample chambers 305, 310). Additionally, the pressure, volume and temperature of the nitrogen in sample chambers 305, 310 may be utilized in equations of state to calculate various sample properties such as, for example, interfacial tension, thermal expansion, compressibility, and phase behavior. Also, a moment of inertia of the sample chambers 305, 310 may be utilized to calculate various sample properties such as, for example, interfacial tension, thermal expansion, compressibility, and phase behavior. The calculated sample properties from sample chambers 305, 310 may be compared to the sample properties obtained from sample chamber 315 (standard un-cushioned sample chamber) for QC.

Regarding a moment of inertia: Assuming the density of the sample and hydraulic fluid (e.g., gas such as nitrogen), the weight and volume of the sample may be calculated by calculating the weight of sample chambers 305, 310. If the density of the sample is unknown, the volume may still be calculable, but with some loss in accuracy. The dimensions, materials of the sample chambers 305, 310 and the type of hydraulic fluid may be converted into a calculation model based on moments and resisting force. A model may include material balance, pre and post job sample bottle weights, and densities of the hydraulic fluid and sample. An improved method may be to weigh sample chambers 305, 310 in such a manner as to capture the distribution of mass within the sample chambers 305, 310. By utilizing two scales and the sample chambers 305, 310 in a horizontal orientation, the distribution of mass becomes apparent.

Because the fluid in sample chamber 315 (standard un-cushioned sample chamber) cools as it is pulled out of the well, the associated pressure drop may result in the fluid developing two phases inside the sample chamber 315, thus there may be a need for homogenization before sample transfer (e.g., transportation to a laboratory for PVT/composition analysis). Therefore, downhole fluid samplers such as single-phase or monophasic samplers (e.g., sample chambers 305, 310) may be utilized. Sample chambers 305, 310 may use gas (e.g., nitrogen) pressure behind pistons 306 to maintain the downhole sample above reservoir pressure while pulling the sample chambers 305, 310 to surface 111 (e.g., FIG. 1). The sample chambers 305, 310 may be designed for reservoir fluids which are likely to precipitate asphaltenes during pressure reduction. For other fluids, sample chambers 305, 310 may facilitate sample transfer and reduce the chance of the transferred fluid not being representative of the fluid in the sampler or in the reservoir. A disadvantage of the one-phase sampler (e.g., sample chambers 305, 310) may be that a bubble point determination cannot be performed on site because the gas buffer (nitrogen cushion) may mask sample behavior (phase behavior). One solution to this limitation is to run sample chamber 315 (standard un-cushioned sample chamber) in tandem to permit a quality check (QC) on one of the fluid samples.

Sample chambers 305, 310 and 315 may comprise probes 307. Probes 307 may be self-contained, self-powered and measure temperature and/or pressure with separate temperature and pressure sensors (e.g., temperature sensor 312, pressure sensor 313). The separate temperature and pressure sensors may allow independent utilization of each sensor.

Probes 307 may include feed through wires 311 that may allow communication (e.g., communication to an analytical instrument) and charging of the probes 307. Feed through wires 311 may extend from within probes 307 to the outside of probes 307, as illustrated in FIG. 3. Probes 307 may be located on the nitrogen filled section 308 of sample chambers 305, 310 (nitrogen-cushioned cylinders) assuming pressure communication and temperature communication across the pistons 306 is sufficient. Alternative to feed through wires 311, probes 307 may wirelessly transmit information across the sample chamber boundary, either acoustically or magnetically. Other forms of wireless communication are also possible. Power could be obtained through the motion of the sample chamber or piezoelectrically or inductively recharged. Alternatively, the probes 307 may be removed during servicing to recharge and communicate data (time, pressure, volume and temperature data of the sample fluid) from memory 303 to a computer and/or analytical device for analysis of the sample fluid.

After the formation testing tool 125 samples formation fluid, the formation testing tool 125 may be brought back to the surface 111 (e.g., via wireline or drill string 110 shown on FIG. 1) the sample chambers 305, 310, and 315 may be removed from the formation testing tool 125 and transported to a laboratory for PVT and composition analyses. The probes 307 may continuously or periodically measure pressure and temperature of the sample fluid from the time the sample was taken downhole to the time the sample chambers 305, 310, and 315 are opened (e.g., opened at a laboratory for analysis). After removal of the sample chambers 305, 310, and 315 from the formation testing tool 125, probes 307 may be connected to a computer (e.g., via plugging into a computer) and data (time, pressure, volume and temperature data of the sample fluid) may be downloaded from memory 303 onto a computer for analysis.

A concern in transporting a downhole fluid sample may be maintaining the integrity of the sample during the transfer operation. This may require that the fluid in the sample chambers 305, 310, and 315 be maintained in a single-phase condition during the entire sample-transport process or, if the sample is in a two-phase condition, that the entire contents of the sample chambers 305, 310, and 315 be transferred. (The sample chambers 305, 310, and 315 may be heated if wax or asphaltenes are present.) As mentioned above, the samples may contain asphaltenes.

Asphaltenes may primarily precipitate as a function of pressure induced changes in a fluid, although, the envelope may have a slight temperature effect. Asphaltenes may precipitate either above the bubble point for a fluid or below the bubble point for a fluid. Therefore, even if a fluid is maintained at a single phase with respect to liquid and gas, there may be a solid asphaltene precipitation phase change.

Also, samples may undergo multiple phase changes as different classes of asphalts are precipitated at different pressures. Asphaltene precipitation may not cause a noticeable volume change of a sample, but has been measured coulimetrically as an exothermic process due to a change in the entropy state of the system and could be noticed with a high resolution temperature measurement as a slight temperature increase (or discontinuity) in what should otherwise be a monotonically decreasing temperature with transit uphold.

Detection of asphaltene precipitation may be augmented if the surface of the temperature sensor 312 were to be prepared with a polar surface capable of nucleating a coating of asphaltenes. A bubble point phase change in contrast may sometimes be associated with a Joule Thompson cooling effect, and therefore may impulse the temperature in the negative direction.

It should be noted that the functional groups attached to the backbone of asphaltene molecules may affect solubility as well. Additionally, multiple asphaltene precipitation points for classes may be contained within a sample. Temperature detection may be augmented with a differential between two temperature sensors 312, one being prepared to accept a film of asphaltenes and the other reference not being prepared. Probes 307 may further include an optical sensor which may also provide discrimination capabilities for phase change, but especially asphaltene precipitation. This detection may also be enhanced if the window surface is prepared for asphaltene precipitation. Optical detection may also be enhanced with differential detection, with one interrogating window surface prepared for precipitation and the other not.

Because valid transfer may be desired to maintain sample quality, one procedure may be to maintain the samples as a single-phase and transfer them in their entirety. An important consideration may be that pressurizing the sample may produce a single-phase condition but may not homogenize the sample; thus, thorough agitation, homogenizing, (by rocking/shaking the cylinder) during the process may be utilized.

Additionally, the samples may not be altered in cases in which the cushion/buffer gas (e.g., nitrogen) is in direct contact with the sample either by leaks of nitrogen across the piston 306. This leaking may be caused by jarring of the sample chambers 305, 310, which may be monitored by movement of pistons 306, as discussed above.

FIG. 4 illustrates an example wireline environment 400. As illustrated, borehole 112 may extend from wellhead 402 into subterranean formation 108 from a surface 111. Generally, borehole 112 may include horizontal, vertical, slanted, curved, and other types of wellbore geometries and orientations.

Formation testing tool 125 may be tethered to vehicle 404 through conveyance 406. Conveyance 406 may be disposed around one or more sheave wheels 408. Derrick 410 may include a load cell (not shown) which determines the amount of pull on conveyance 406 at surface 111. Information handling system 412 may control a safety valve (not illustrated) which controls the hydraulic pressure that drives drum 414 on vehicle 404, which may reel up and/or release conveyance 406 which may move formation testing tool 125 up and/or down. The safety valve may be adjusted to a pressure such that sheave wheel 408 may only impart a small amount of tension to conveyance 406 and/or over and above the tension necessary to retrieve conveyance 406 and/or formation testing tool 125. The safety valve is typically set a few hundred pounds above the amount of desired safe pull on conveyance 406 such that once that limit is exceeded, further pull on conveyance 406 may be prevented.

Conveyance 406 may individually be a wireline, slickline, coiled tubing, pipe, or the like, which may provide mechanical suspension as well as electrical conductivity for formation testing tool 125. Where it may provide electrical conducting, conveyance 406 may comprise an inner core of a plurality of electrical conductors covered by an insulating wrap. An inner and outer steel armor sheath may be disposed around the conductors. The electrical conductors may be used for communicating power and telemetry between vehicle 404 (or other equipment) and formation testing tool 125.

Accordingly, this disclosure describes systems and methods that may be used for corrosion detection of downhole tubulars. The systems and methods may further be characterized by one or more of the following statements:

Statement 1: A method comprising: lowering a formation testing tool into a subterranean formation, wherein the formation testing tool comprises memory, a pump, a formation probe, at least two sample chambers, wherein the at least two sample chambers comprise probes to measure pressure and temperature; extracting a fluid from the subterranean formation with the pump and the formation probe; flowing the fluid into the at least two sample chambers with the pump; storing pressure and temperature data of the fluid in the memory; and removing the at least two sample chambers from the formation testing tool.

Statement 2: The method of statement 1, wherein the at least two sample chambers comprise a cushioned sample chamber comprising a nitrogen section and a fluid sample section, and an un-cushioned sample chamber comprising a fluid sample section.

Statement 3: The method of statement 1 or statement 2, wherein the memory comprises volatile memory or nonvolatile memory.

Statement 4: The method of any preceding statement, wherein the probes comprise feed through wires configured to allow communication and charging of the probes.

Statement 5: The method of any preceding statement, further comprising continuously monitoring pressure and temperature of the fluid within the un-cushioned sample chamber and the cushioned sample chamber from a time of recovery of the fluid to a time of opening the un-cushioned sample chamber and the cushioned sample chamber.

Statement 6: The method of any preceding statement, further comprising determining fluid properties of the fluid within the cushioned sample chamber with a moment of inertia.

Statement 7: The method of any preceding statement, further comprising determining fluid properties of the fluid within the cushioned sample chamber utilizing a pressure, volume and temperature of the nitrogen.

Statement 8: The method of any preceding statement, wherein the cushioned sample chamber comprises a piston.

Statement 9: The method of any preceding statement, wherein the piston comprises a magnet.

Statement 10: The method of any preceding statement, wherein the determining fluid properties of the fluid within the cushioned sample chamber comprises utilizing a position of the magnet relative to each end of the cushioned sample chamber.

Statement 11: A method comprising: lowering a formation testing tool into a subterranean formation, wherein the formation testing tool comprises memory, a pump, a formation probe, an un-cushioned sample chamber and a cushioned sample chamber, wherein the un-cushioned sample chamber and the cushioned sample chamber each comprise probes to measure pressure and temperature; wherein the cushioned sample chamber further comprises a piston; extracting a fluid from the subterranean formation with the pump and the formation probe; flowing the fluid into the un-cushioned sample chamber and the cushioned sample chamber with the pump; storing pressure and temperature data of the fluid in the memory; removing the un-cushioned sample chamber and the cushioned sample chamber from the formation testing tool; transporting the un-cushioned sample chamber and the cushioned sample chamber to a lab; determining fluid properties of the fluid at a downhole pressure and temperature; and comparing the fluid properties from the un-cushioned sample chamber to the cushioned sample chamber to provide quality control of the fluid.

Statement 12: The method of statement 11, wherein the fluid properties comprise at least one property selected from the group consisting of interfacial tension, thermal expansion, compressibility, and phase behavior.

Statement 13: The method of statement 11 or 12, wherein the volume of the un-cushioned sample chamber and the cushioned sample chamber each range from about 0.5 liters to about 2 liters.

Statement 14: The method of any one of statements 11-13, further comprising pressurizing the cushioned sample chamber with about 3,000 psi to about 6,000 psi of nitrogen.

Statement 15: The method of any one of statements 11-14, wherein the cushioned sample chamber comprises a single phase of the fluid.

Statement 16: The method of any one of statements 11-15, further comprising homogenizing the fluid within the un-cushioned sample chamber and the cushioned sample chamber.

Statement 17: A formation testing tool comprising: a pump; a formation probe; a sample chamber; a pressure sensor to measure pressure in the sample chamber; a temperature sensor to measure temperature in the sample chamber; and a memory to record measurements from the pressure sensor and the temperature sensor.

Statement 18: The formation testing tool of statement 17, wherein the pressure sensor and the temperature sensor are configured to continuously monitor pressure and temperature of the sample in the sample fluid section from a time of recovery to a time of opening the sample chamber.

Statement 19: The formation testing tool of statement 17, wherein the sample chamber is un-cushioned sample chamber comprising a nitrogen section and a sample fluid section.

Statement 20: The formation testing tool of statement 18 or statement 19, wherein the nitrogen section and the sample fluid section are separated by a piston.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method comprising:
lowering a formation testing tool into a subterranean formation, wherein the formation testing tool comprises memory, a pump, a formation probe, at least two sample chambers, wherein the at least two sample chambers comprise probes to measure pressure and temperature and wherein the at least two sample chambers comprise a cushioned sample chamber comprising a nitrogen section and a fluid sample section, and an un-cushioned sample chamber comprising a fluid sample section;
extracting a fluid from the subterranean formation with the pump and the formation probe;
flowing the fluid into the at least two sample chambers with the pump;
storing pressure and temperature data of the fluid in the memory; and
removing the at least two sample chambers from the formation testing tool.

2. The method of claim 1, further comprising continuously monitoring pressure and temperature of the fluid within the un-cushioned sample chamber and the cushioned sample chamber from a time of recovery of the fluid to a time of opening the un-cushioned sample chamber and the cushioned sample chamber.

3. The method of claim 1, wherein the memory comprises volatile memory or non-volatile memory.

4. The method of claim 1, wherein the probes comprise feed through wires configured to allow communication and charging of the probes.

5. The method of claim 4, further comprising determining fluid properties of the fluid within a cushioned sample chamber with a moment of inertia.

6. The method of claim 4, further comprising determining fluid properties of the fluid within the cushioned sample chamber utilizing a pressure, volume and temperature of the nitrogen.

7. The method of claim 6, wherein the cushioned sample chamber comprises a piston.

8. The method of claim 7, wherein the piston comprises a magnet.

9. The method of claim 8, wherein the determining fluid properties of the fluid within the cushioned sample chamber comprises utilizing a position of the magnet relative to each end of the cushioned sample chamber.

10. A method comprising:
lowering a formation testing tool into a subterranean formation, wherein the formation testing tool comprises memory, a pump, a formation probe, an un-cushioned sample chamber, and a cushioned sample chamber, wherein the un-cushioned sample chamber and the cushioned sample chamber each comprise probes to measure pressure and temperature; wherein the cushioned sample chamber further comprises a piston;
extracting a fluid from the subterranean formation with the pump and the formation probe;
flowing the fluid into the un-cushioned sample chamber and the cushioned sample chamber with the pump;
storing pressure and temperature data of the fluid in the memory;
removing the un-cushioned sample chamber and the cushioned sample chamber from the formation testing tool;
transporting the un-cushioned sample chamber and the cushioned sample chamber to a lab;
determining fluid properties of the fluid at a downhole pressure and temperature; and
comparing the fluid properties from the un-cushioned sample chamber to the cushioned sample chamber to provide quality control of the fluid.

11. The method of claim 10, wherein the fluid properties comprise at least one property selected from the group consisting of interfacial tension, thermal expansion, compressibility, and phase behavior.

12. The method of claim 10, wherein the volume of the un-cushioned sample chamber and the cushioned sample chamber each range from about 0.5 liters to about 2 liters.

13. The method of claim 10, further comprising pressurizing the cushioned sample chamber with about 3,000 psi to about 6,000 psi of nitrogen.

14. The method of claim 10, wherein the cushioned sample chamber comprises a single phase of the fluid.

15. The method of claim 10, further comprising homogenizing the fluid within the un-cushioned sample chamber and the cushioned sample chamber.

16. A formation testing tool comprising:
a pump;
a formation probe;
at least two sample chambers, wherein the at least two sample chambers comprise a cushioned sample chamber comprising a nitrogen section and a fluid sample section, and an un-cushioned sample chamber comprising a fluid sample section;
a pressure sensor to measure pressure in the sample chamber;
a temperature sensor to measure temperature in the sample chamber; and
a memory to record measurements from the pressure sensor and the temperature sensor.

17. The formation testing tool of claim 16, wherein the pressure sensor and the temperature sensor are configured to continuously monitor pressure and temperature of the sample in the sample fluid section from a time of recovery to a time of opening the sample chamber.

18. The formation testing tool of claim 16, wherein the nitrogen section and the sample fluid section are separated by a piston.

19. A method comprising:
lowering a formation testing tool into a subterranean formation, wherein the formation testing tool comprises memory, a pump, a formation probe, at least two sample chambers, wherein the at least two sample chambers comprise probes to measure pressure and temperature and wherein the at least two sample chambers comprise a cushioned sample chamber comprising a nitrogen section and a fluid sample section;
extracting a fluid from the subterranean formation with the pump and the formation probe;
flowing the fluid into the at least two sample chambers with the pump;
storing pressure and temperature data of the fluid in the memory;
determining fluid properties of the fluid utilizing a pressure, volume and temperature of the nitrogen; and
removing the at least two sample chambers from the formation testing tool.

* * * * *